(12) United States Patent
Chirayil et al.

(10) Patent No.: US 9,839,587 B2
(45) Date of Patent: Dec. 12, 2017

(54) TREATED PLATY SUBSTRATES

(71) Applicant: BASF CORPORATION, Florham Park, NJ (US)

(72) Inventors: Thomas Chirayil, Danbury, CT (US); David A. Yale, Bethel, CT (US); Betty Aucar, Ossining, NY (US); Matthew Delfico, Danbury City, CT (US)

(73) Assignee: BASF CORPORATION, Florham Park, NJ (US)

( * ) Notice: Subject to any disclaimer, the term of this patent is extended or adjusted under 35 U.S.C. 154(b) by 373 days.

(21) Appl. No.: 13/794,897

(22) Filed: Mar. 12, 2013

(65) Prior Publication Data

US 2013/0259914 A1 Oct. 3, 2013

Related U.S. Application Data (60) Provisional application No. 61/609,758, filed on Mar. 12, 2012, provisional application No. 61/612,614, filed on Mar. 19, 2012.

(51) Int. Cl.
*A61K 8/02* (2006.01)
*A61K 8/26* (2006.01)
(Continued)

(52) U.S. Cl.
CPC .......... *A61K 8/0233* (2013.01); *A61K 8/0254* (2013.01); *A61K 8/0258* (2013.01); *A61K 8/26* (2013.01); *A61K 8/44* (2013.01); *A61Q 1/02* (2013.01); *A61Q 1/04* (2013.01); *A61Q 1/06* (2013.01); *A61Q 1/10* (2013.01); *A61Q 1/12* (2013.01); *A61Q 3/02* (2013.01); *A61Q 5/02* (2013.01); *A61Q 5/06* (2013.01); *A61Q 11/00* (2013.01); *A61Q 15/00* (2013.01); *A61Q 17/04* (2013.01); *C09C 1/405* (2013.01);
(Continued)

(58) Field of Classification Search
CPC .. A61K 8/0254; A61K 2800/651; A61Q 1/02; A61Q 1/04; A61Q 1/06; A61Q 17/04
See application file for complete search history.

(56) References Cited

U.S. PATENT DOCUMENTS

| 4,640,943 | A | | 2/1987 | Meguro et al. |
| 5,326,392 | A | * | 7/1994 | Miller .................... A61K 8/44 |
| | | | | 106/417 |

(Continued)

FOREIGN PATENT DOCUMENTS

| EP | 1366737 A1 | 3/2003 |
| JP | 08-067609 | 3/1996 |

(Continued)

OTHER PUBLICATIONS

English translation of Nagai et al. (JP 2007-176937 A; published Jul. 12, 2007) by Schreiber Translations, Inc. dated Dec. 2015, pp. 1-58.*

(Continued)

*Primary Examiner* — Michael B. Pallay
(74) *Attorney, Agent, or Firm* — Foley & Lardner LLP (57) ABSTRACT

Provided is a treated platy substrate, a method of making it, and methods of using it. The substrate can be synthetic mica, optionally comprising metal-oxide layers. The treated platy substrate is useful in cosmetic compositions.

6 Claims, 4 Drawing Sheets

Synthetic mica with 5% Lauroyl Lysine ( x 5000)

(51) Int. Cl.
*A61K 8/44* (2006.01)
*A61Q 1/02* (2006.01)
*C09C 1/40* (2006.01)
*A61Q 1/04* (2006.01)
*A61Q 1/06* (2006.01)
*A61Q 1/10* (2006.01)
*A61Q 1/12* (2006.01)
*A61Q 3/02* (2006.01)
*A61Q 5/02* (2006.01)
*A61Q 5/06* (2006.01)
*A61Q 11/00* (2006.01)
*A61Q 15/00* (2006.01)
*A61Q 17/04* (2006.01)

(52) U.S. Cl.
CPC .. *A61K 2800/412* (2013.01); *A61K 2800/612* (2013.01); *A61K 2800/622* (2013.01); *A61K 2800/651* (2013.01); *C01P 2004/03* (2013.01); *C01P 2006/60* (2013.01)

(56) References Cited

U.S. PATENT DOCUMENTS

| | | | | |
|---|---|---|---|---|
| 5,908,631 | A | * | 6/1999 | Arnaud .................... A61K 8/37 424/401 |
| 6,004,584 | A | | 12/1999 | Peterson et al. |
| 6,780,826 | B2 | | 8/2004 | Zhang et al. |
| 7,678,750 | B2 | | 3/2010 | Hoffmann et al. |
| 2004/0223929 | A1 | * | 11/2004 | Clapp .................. A61K 8/0237 424/63 |
| 2005/0142084 | A1 | * | 6/2005 | Ganguly ................ A61K 8/26 424/63 |
| 2009/0196841 | A1 | | 8/2009 | Song et al. |
| 2010/0322981 | A1 | | 12/2010 | Bujard et al. |
| 2011/0048284 | A1 | | 3/2011 | Choi et al. |
| 2013/0259914 | A1 | * | 10/2013 | Chirayil ................. A61K 8/26 424/401 |

FOREIGN PATENT DOCUMENTS

| | | | |
|---|---|---|---|
| JP | 2005-298385 | 10/2005 | |
| JP | 2007176937 A | * 7/2007 | ............... A61K 8/25 |
| JP | 20070176937 A | 7/2007 | |
| KR | 1020050093557 A | 9/2005 | |
| KR | 100817525 | 3/2008 | |
| WO | WO-2011/095447 | 8/2011 | |

OTHER PUBLICATIONS

Uzunian, G. et al., "Improving eye shadow compressibility: the effects of lauroyl lysine coating on platy substrates". Cosmetics & Toiletries. 1993, vol. 108. No. 2, pp. 93-98. See the paragraph of "Formulation" and table I.

Office Action in JP Application No. 2015-500512, dated Nov. 29, 2016 (English translation included—7 pages).

First Office Action received for Chinese Patent Application No. 20130014108.X dated Apr. 15, 2016, 17 pages with English translation.

* cited by examiner

FIG. 1

Uncoated synthetic Mica ( x 5000)

*Prior Art*

FIG. 2

Synthetic mica with 5% Lauroyl Lysine ( x 5000)

FIG. 3

Synthetic mica blended with 5% Lauroyl Lysine ( x 10,000)

FIG. 4

TREATED PLATY SUBSTRATES

CROSS-REFERENCE TO RELATED APPLICATIONS

The benefit of the filing dates of U.S. Provisional Patent Application Nos. 61/609,758, filed Mar. 12, 2012 and 61/612,614, filed Mar. 19, 2012, are hereby claimed. The entire disclosures of the aforesaid applications are incorporated herein in their entirety by reference.

BACKGROUND

Platy pigments are composed of a plurality of laminar platelets coated with one or more reflecting/transmitting layers. Typically, effect pigments are a laminar platy substrate such as natural mica or glass flake that has been coated with a metal oxide layer. A description of effect pigments' properties can be found in the Pigment Handbook, Volume I, Second Edition, pp. 829-858, John Wiley & Sons, NY 1988, which is incorporated herein by reference. If colorless metal oxides are used to coat the laminar platy substrate, effect pigments exhibit pearl-like luster as a result of reflection and refraction of light, and depending on the thickness of the metal oxide layer, they can also exhibit interference color effects. If colored metal oxides are used, the observed effects depend on reflection, refraction and absorption.

Platy pigments, such as effect pigments (also known as pearlescent pigments or nacreous pigments), are used to impart a pearlescent luster, metallic luster and/or multi-color effect approaching iridescence, to a material. It is, for instance, common to include platy pigments in cosmetic and personal care compositions, to contribute to or provide color, luster and/or pleasing tactile properties. Natural mica and metal oxide-coated natural mica have a surface hydrophilicity character that may not be suitable for interaction with skin. In addition, the hydrophilicity can affect the distribution or dispersion of the pigment in a cosmetic composition.

Surface modification of natural mica or metal oxide-coated natural mica with hydrophobic materials is known. See, for instance, U.S. Pat. Nos. 4,640,943; 5,326,392; and 6,780,826; and U.S. Pat. App. Pub. 2004/0223929.

There is an on-going need in the art for platy substrates and platy pigments with improved properties.

SUMMARY

The following embodiments meet and address these needs. The following summary is not an extensive overview. It is intended to neither identify key or critical elements of the various embodiments, nor delineate their scope.

Provided is a treated platy substrate comprising a platy substrate coated with Nϵ-lauroyl-L-lysine, wherein the platy substrate is one or more of synthetic mica; metal oxide-coated synthetic mica; platy aluminum oxide flakes; metal oxide-coated platy aluminum oxide flakes; silicon dioxide flakes; metal oxide-coated silicon dioxide flakes; glass flakes; metal oxide-coated glass flakes; perlite flakes; and metal oxide-coated perlite flakes. The Nϵ-lauroyl-L-lysine coating can be present on the surface of the platy substrate in the range of about 0.5% to about 15% weight of the platy substrate. In an embodiment, the Nϵ-lauroyl-L-lysine coating can be present on the surface of the platy substrate in the range of about 4% to about 6% weight of the platy substrate, or about 4.5% weight of the platy substrate. The treated platy substrate can comprise less than or equal to 1 ppm lead. The treated platy substrate can have a hydrophobic contact angle of greater than 90° or at least about 130°. The treated platy substrate can have one or more of: improved hardness, improved compressibility, and improved masking properties.

Also provided is a cosmetic composition comprising the treated platy substrate. The cosmetic composition can further comprise a particulate component having a gritty feeling and wherein the treated platy substrate is present in an amount sufficient to mask the gritty feeling.

A method of preparing the treated platy substrate is also provided. The method comprises contacting a platy substrate in an aqueous dispersion with a Nϵ-lauroyl-L-lysine solution to form a reaction mixture, wherein the pH of the reaction is maintained at about 5 to 7. The contacting step is under reaction conditions that result in precipitation of the Nϵ-lauroyl-L-lysine onto the surface of a platy substrate in the reaction mixture. Nϵ-lauroyl-L-lysine can be precipitated at about 0.5% to 15.0% by weight of the platy substrate. The rate of addition of Nϵ-lauroyl-L-lysine can be about 0.15-1.0 milligrams Nϵ-lauroyl-L-lysine per gram platy substrate per minute. The platy substrate is one or more of synthetic mica; metal oxide-coated synthetic mica; platy aluminum oxide flakes; metal oxide-coated platy aluminum oxide flakes; silicon dioxide flakes; metal oxide-coated silicon dioxide flakes; glass flakes; metal oxide-coated glass flakes; perlite flakes; and metal oxide-coated perlite flakes.

BASF CHIONE™ M SVA is a novel performance mineral composed of Synthetic Fluorophlogopite, commonly known as synthetic mica, coated with lauroyl lysine. The resulting powder is very white and have a velvety texture, which can enhance the feel of both anhydrous and hydroalchoholic formulations. This highly lubricious additive is suitable for all cosmetic applications, including eye and lip area use. Its very white appearance is also suited for skin car formulations, where the neutral color will not impact the base color of the formulated cosmetic. Exemplary formulations demonstrating the use of CHIONE™ M SVA are provided herein. These examples are not meant to be limiting in any way, and one skilled in the art will readily find many other applications and combinations of cosmetic ingredients, colorants, and the above disclosed performance mineral.

BRIEF DESCRIPTION OF THE DRAWINGS

For the purpose of illustrating the various compositions and methods, there are depicted in the drawings certain embodiments. However, the compositions and their methods of use are not limited to the precise arrangements and instrumentalities of the embodiments depicted in the drawings.

DETAILED DESCRIPTION

There is a need in the art to provide platy substrates with improved properties. Provided herein is a treated platy substrate that meets these needs. The treated platy substrate disclosed has surface modification resulting in a hydrophobic surface. The treated platy substrate can exhibit good oil absorption, which can benefit cosmetic formulations, such a lipsticks. Cosmetic compositions comprising the treated platy substrate exhibit very smooth, creamy skin feeling, and provides good skin adhesion. Notably, the treated platy substrate disclosed herein has improved transparency in cosmetic compositions compared to compositions comprising talc or lauroyl lysine treated natural mica. The treated platy substrate can hide or mask the gritty feeling of particulate components, for instance, 5 micron REFLECKS, in a cosmetic composition. Additionally, the treated platy substrate can possess an improved compressibility profile, including compressibility at lower pressures, and improved hardness and uniformity in pressed compositions. Further provided are a method of preparing the treated platy substrate, and compositions comprising the treated platy substrate.

The treated platy substrate comprises a platy substrate that comprises a coating of compound I:

wherein m is an even number from 8 to 18 and n is 3 or 4. In an embodiment, the platy substrate is coated with compound I wherein n is 3. In an aspect, the platy substrate is coated with compound I wherein n is 3 and m is 18. In an embodiment, the compound is Nϵ-lauroyl-L-lysine. The coating acts to modify the surface of the platy substrate such that the treated platy substrate has improved properties.

Methods of preparing compound I, including Nϵ-lauroyl-L-lysine, are known in the art. See, for instance, U.S. Pat. Nos. 4,640,943 and 5,326,392. In addition, Nϵ-lauroyl-L-lysine is commercially available, for instance, Amihope® LL from Ajinomoto NA (Fort Lee, N.J.).

A "platy substrate" refers to a lamellar material having a high aspect ratio (ratio of average particle size to particle thickness). Examples of platy materials useful as substrates include synthetic mica; platy aluminum oxide flakes; silicon dioxide flakes; glass flakes; and perlite flakes. As used herein, "synthetic mica" refers to synthetic fluorphlogopite. Metal oxide-coated platy materials, such as titanium dioxide ($TiO_2$)-coated synthetic mica, can also be used. Other metal oxides for coating the platy substrate include $Fe_2O_3$, $Fe_3O_4$, $SiO_2$, bismuth oxychloride, and combinations thereof. Excluded platy materials are: talc; natural mica including, but not limited to, natural muscovite, natural sericite, and natural phlogopite; iron oxide coated natural mica; titanium dioxide natural mica; and chromium oxide coated natural mice. In an embodiment, the substrate is synthetic mica. Synthetic mica comprising a low lead (Pb) level of less than 3 ppm Pb, less than or equal to 1 ppm Pb or less than or equal to 0.5 ppm Pb can be used. The low Pb synthetic mica can be uncoated, or it can coated with a metal oxide, such as titanium dioxide, or multi-layers of metal oxide, such as alternating layers of titanium dioxide and silicon dioxide or an iron oxide.

Platy materials comprising metal oxide layers can be formed by any process known in the art. It can be accomplished, as one example, by precipitating a metal ion with hydroxide onto laminar platy substrate, such as synthetic mica, and thereafter, calcining the coated particulates to provide metal oxide-coated flake-form pigment. Other coating procedures, such as for example, chemical vapor deposition processes, can also be used to prepare metal oxide-coated platy substrates useful in the claimed composition. In an embodiment, the substrate comprises or consists of $TiO_2$-coated synthetic mica. Metal oxide-coated platy substrates further comprising an organic colorant can be used. Colorants include, but are not limited to, absorption colorants, D&C colors, and FD&C colors. In an embodiment, the colorant is deposited with compound I, such as Nϵ-lauroyl-L-lysine, on the metal oxide-coated platy substrate.

The average particle size of the platy substrates can vary from an average of about 3 micrometers to an average of about 100 micrometers (μm), although smaller flakes of down to about 1 μm) and less or larger flakes of up to 150 μm or more can also be used if desired. The platy substrate can have a thickness of about 0.1 to 10 μm and an aspect ratio (average particle size/thickness) of at least about 10 and up to about 200.

Particle size distribution of the platy substrate is not critical to the preparation of the treated platy substrate. Particle size distribution can be important in subsequent uses of the treated platy substrate. For cosmetic applications, platy substrates having a narrow particle size distribution can be used. Common ranges include 5-25 micrometers (μm) with 10 μm average; 1-45 μm with 20 μm average, 20-70 μm with 50 μm average; and 15-90 μm, with 50 μm average. In an embodiment, a platy substrate can have a particle size distribution of about D10=2-4 micrometers (μm); D50=6-8 μm; D90=15-20 μm. In another embodiment, a platy substrate can have a particle size distribution of D10=3.4 micrometers (μm); D50=8.7 μm; and D90=9.7 μm.

Effect pigments comprising synthetic mica as substrates are commercially available and can be treated according the method disclosed to prepare treated platy substrates. Synthetic mica based pigments include those available from BASF Corporation (Florham Park, N.J.) under the trade name CHIONE™. Other commercially available synthetic mica based pigments include Fiesta Color Effect Pigments (Impact Colors, Inc., Newark, Del.) and TIMIRON® Ice Crystal and TIMIRON® Synwhite 40 from EMD Chemicals Inc (Gibbstown, N.J.). Platy material that is not commercially available can also be treated in accordance with the disclosed method.

In an embodiment, the treated platy substrate comprises about 90% to 96% weight synthetic mica with an about 4% to 10% wt. Nϵ-lauroyl-L-lysine coating, or about 94% to 96% weight synthetic mica with an about 4% to 6% wt. Nϵ-lauroyl-L-lysine coating, or about 95.5% weight synthetic mica with about 4.5% wt. Nϵ-lauroyl-L-lysine coating. The particle size of the treated platy substrate in this embodiment can be in the range of 5-25 micrometers (μm) with an about 10 μm average. In one aspect, the treated synthetic mica can have a particle size distribution of about D10=2-4 micrometers (μm); D50=6-8 μm; D90=15-20 μm. In another embodiment, the treated synthetic mica can have a particle size distribution of D10=3.4 micrometers (μm); D50=8.7 μm; and D90=9.7 μm. The whiteness of the treated platy substrate can be equal to or greater than 50, 60 or 70 on the whiteness index (per ASTM E313).

The compound is coated onto the surface of the platy substrate by precipitation. In general, the procedure for precipitating compound I, and in particular, Nϵ-lauroyl-L-lysine, is carried by adding, with stirring, either an acidic or alkaline solution of the compound to an aqueous dispersion of platy substrate. The alkaline solution can be 3.5% sodium hydroxide. Alkali or acid is then added to bring the pH into the range of about 5-7 or of about 5.8 to 6.2. The precipitation reaction can be carried out at ambient temperature. The compound precipitates out of solution under the conditions of the reaction medium, and on to the platy substrate surfaces, thereby forming a coating on the platy substrate surface. After the precipitation reaction, the coated platy substrate is washed several times and dried by any method known in the art. The resulting coated platy substrate can be sieved, such as through a #200 mesh screen.

Variables in the method of preparing the treated platy substrate include pH, temperature, concentrations, and addition rates. These variables can be adjusted by the skilled artisan within the disclosed ranges as necessary for a combination of compound and platy substrate.

The compound, such as Nϵ-lauroyl-L-lysine, can be deposited on the platy substrate at concentrations in the range of about 0.5%-20.0%, about 0.5% to 15.0%, about 1.0% to 15.0%, about 4% to about 12%, about 4.5% to 10.0%, about 4% to about 6%, or about 4.5% on the platy substrate. The rate of compound addition to the platy substrate dispersion can be about 0.10-1.50 mg. compound per g. substrate per minute. The skilled artisan can readily select an addition rate that is convenient and effective. An addition rate can be about 0.15-1.0 mg. compound per g. substrate per minute. An addition rate can be about 0.15-1.0 mg. Nϵ-lauroyl-L-lysine per g. synthetic mica per minute.

The pH of the solution during lauroyl lysine addition can be varied or held constant over the range of 5-7. A pH range of about 5.6 to 6.2 can be used for both constant pH procedures and for procedures of variable pH.

The precipitation reaction can be carried out at any temperature from about 15° C. to 80° C. It can be convenient to use an ambient temperature, e.g., 15° C. to 30° C. or 20° C. to 30° C.

In some cases, the precipitation of the compound is carried out with a calcium salt, such as calcium chloride, in the stirred aqueous platy substrate dispersion. In these cases, the aqueous platy substrate dispersion comprises calcium chloride in the range of about 0.25-1.0 mole, or about 0.5 mole, for each mole of Nϵ-lauroyl-L-lysine added. The effect of the calcium chloride is a salting-out effect. That is, the salting out may speed up or facilitate the precipitation, and it beneficially affects the character of the precipitate and the treated platy substrate. A salt with the compound is essentially not formed.

The platy substrate is generally dispersed in an aqueous medium at about 4% to 20% wt./wt., before the start of the treatment reaction. Considerations for selecting the wt. % include formation of a good dispersion and the ability to achieve adequate stirring during precipitation. When synthetic mica is the platy substrate, a dispersion comprising about 5 wt./wt to about 15% wt./wt or 8% wt./wt to about 12% wt./wt synthetic mica can be used.

The treated platy substrate disclosed can be used in any application benefiting from the properties the treated platy substrates possess. These properties include for example: improved hydrophobic surface such as a contact angle greater than 90°, greater than 105°, or greater than 130°, or between about 135° to 140°; improved compressibility, e.g., more uniform compression compared to non-treated substrate and compression at lower pressures; smooth skin feeling; high oil absorption; improved transparency that reduces dirty mass tones of prior art platy substrates, such as talc or lauroyl lysine coated natural mica in cosmetic compositions; able to hide or mask the gritty feeling of other pigments, such as 5 micron REFLECKS platy pigment, in compositions better than, for instance, treated natural mica. Treated synthetic mica can also exhibit increased hardness in a pressed sample, relative to treated natural mica in a sample pressed under the same conditions as the treated synthetic mica and as measured on a pressed sample using a durometer. The increased hardness of treated synthetic mica is least about 1%, at least about 3% or at least about 5%, relative to treated natural mica. Treated synthetic mica can have a hardness of equal to greater than about 60, about 61, about 62 or about 63, on a hardness scale of 0 to 100, as measured using a durometer. Applications that can benefit from one or more of these properties include, but are not limited to, cosmetics, paints, ink jet printing, for dyeing textiles, for pigmenting coatings (paints), printing inks, plastics, glazes for ceramics and glass, and the like.

The treated platy substrate can be part of a cosmetic composition. The cosmetic composition can comprise non-treated platy substrates or natural mica platy substrates, or the cosmetic composition can exclude non-treated platy substrates and/or natural mica platy substrates. The form of the cosmetic composition can be any form normally used for cosmetics such as cream, emulsion, foam, gel, lotion, milk, mousse, ointment, paste, powder, spray, or suspension. The cosmetic composition can be any colored cosmetic used on the skin, hair, eyes, or lips, such as concealing sticks, foundation, stage make-up, mascara (cake or cream), eye shadow (liquid, pomade, powder, stick, pressed or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, perfume lotion, and shampoos of all types (gel or liquid). In addition, the claimed compositions can be used in shaving cream (concentrate for aerosol, brushless, lathering), hair groom, cologne stick, cologne, cologne emollient, bubble bath, body lotion (moisturizing, cleansing, analgesic, astringent), after shave lotion, after bath milk and sunscreen lotion. For a review of cosmetic applications, see COSMETICS: SCIENCE AND TECHNOLOGY, 2nd Ed., Eds: M. S. Balsam and Edward Sagarin, Wiley-Interscience (1972), and deNavarre, THE CHEMISTRY AND SCIENCE OF COSMETICS, 2nd Ed., Vols. 1 and 2 (1962), Van Nostrand Co. Inc., Vols. 3 and 4 (1975), Continental Press, both of which are hereby incorporated by reference.

The amount of the treated platy substrate present in a cosmetic composition is dependent on the cosmetic being created and the final form of the cosmetic. One skilled in the art will be able to determine the appropriate amount of pigment to use based upon the desired properties of the cosmetic formulation; however, a cosmetic composition can comprise from about 0.005 to 99.9%, about 0.05 to about 50%, or about 0.1 to about 10% by weight of the claimed treated platy substrate, based on the total weight of the cosmetic composition.

The cosmetic composition optionally comprises at least one cosmetically acceptable auxiliary agent. Cosmetically acceptable auxiliary agents include, but are not limited to, carriers, excipients, emulsifiers, surfactants, preservatives, fragrances, perfume oils, thickeners, polymers, gel formers, dyes, absorption pigments, photoprotective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous, or antiallergic active ingredients and mixtures thereof. Cosmetic formulations are known in the art. See, for instance, US Publication Nos. 20080196847 and 20100322981.

In the following exemplary cosmetic compositions shown in Tables 1-15, "Chione™ M SVA" refers to the M-fraction of Chione™ synthetic mica treated with lauroyl lysine in accordance with the disclosure. Chione™ M SVA comprises about 94% to 96% weight synthetic mica with an about 4% to 6% wt. Nϵ-lauroyl-L-lysine coating, and has a particle size distribution of D10=3.4 micrometers (μm); D50=8.7 μm; and D90=9.7 μm.

An exemplary sun protection composition is shown in Table 1.

TABLE 1

| Phase | Ingredients | % w/w |
|---|---|---|
| A. | Deionized (DI) Water (q.s. to 100%) | 45.30 |
|  | D-Panthenol 75W (Panthenol)[1] | 1.00 |
|  | Pluracare ® E 400 NF (PEG-8)[1] | 2.50 |
|  | Edeta ® BD (Disodium EDTA)[1] | 0.10 |
|  | Luvigel ® STAR (Polyurethane-39)[1] | 2.50 |
| B. | Uvinul ® T 150* (Octyltriazone)[1] | 2.00 |
|  | Tinosorb ® S* (Bemotrizinol)[1] | 3.00 |
|  | Propylheptyl Caprylate (CETIOL SENSOFT)[2] | 5.00 |
|  | Dicaprylyl Carbonate (CETIOL CC)[2] | 5.00 |
| C. | Cremophor ® A 25 (Ceteareth-25)[1] | 2.50 |
|  | Cremophor ® GS 32 (Polyglyceryl-3 Distearate)[1] | 2.50 |
|  | Cremophor ® WO-7(PEG-7 Hydrogenated Castor Oil)[1] | 0.50 |
|  | Stearyl Alcohol (LANETTE 18)[2] | 2.50 |
|  | Dimethicone (DOW CORNING 200 FLUID 50 CST)[3] | 1.50 |
|  | Luvitol ® Lite (Hydrogenated Polyisobutene)[1] | 1.50 |
|  | Vitamin E Acetate Care (Tocopherol Acetate)[1] | 0.50 |
|  | Bisabolol Racemic (Bisabolol)[1] | 1.00 |
| D. | DI Water | 10.00 |
|  | Tinosorb ® M* (Bisoctrizole)[1] | 10.00 |
| E. | DI Water | 10.00 |
|  | Chione ™ M SVA[1] | 0.75 |
|  | MultiReflections ™ Soft Sparkle Orchid 580P (Mica (and) Titanium Dioxide (and) Silica)[1] | 1.75 |
| F. | Fragrance (ORANGE NECTAR FRAG. AD78-00997)[4] | 0.20 |
|  | Preservatives | q.s. |

[1]BASF
[2]Cognis
[3]Dow Corning Corporation
[4]Ungerer & Company

The sun protection composition can be prepared according to the following steps.
I. Combine Phase A and heat to 75-80° C.
II. Pre-mix Phase B and heat to 75-80° C.
III. Combine Phase C and heat to 75-80° C.
IV. Add Phase B to Phase C while at 75-80° C. and mix well.
V. Add Phase BC to Phase A and homogenize for 2-3 minutes while at 75-80° C. at low speed.
VI. Transfer to sweep mixing and start cooling.
VII. Pre-mix Phase D and add to the batch at 50° C. or below.
VIII. Pre-mix Phase E and add to the batch, then homogenize until uniform.
IX. Add Phase F one by one and mix well, then stop.

An exemplary talc free face powder composition is shown in Table 2.

TABLE 2

| Phase | Ingredients | % w/w |
|---|---|---|
| A. | Chione ™ M SVA[1] (q.s. to 100%) | 36.500 |
|  | Flamenco ® Silk Gold 230M (Mica (and) Titanium Dioxide)[1] | 18.500 |
|  | Z-Cote ® (Zinc Oxide)[1] | 15.000 |
|  | Chroma-Lite ® Brown CL4509 (Mica (and) Bismuth Oxychloride (and) Iron Oxides)[1] | 20.000 |
|  | Boron Nitride Powder (Boron Nitride)[2] | 5.000 |
| B. | Luvitol ® Lite (Hydrogenated Polyisobutene)[1] | 2.500 |
|  | Octyldodecyl Neopentanoate (Elefac I-205)[3] | 2.500 |
|  | Antioxidants | q.s. |
|  | Preservatives | q.s. |

[1]BASF
[2]ESK Ceramics
[3]Alzo Internation, Inc.

The face powder composition can be prepared according to the following steps.
I. Thoroughly blend Phase A in appropriate dry blending/dispersing equipment.
II. Pre-disperse Phase B and spray into Phase A.
III. Pulverize and package into appropriate containers.

An exemplary concealer stick composition is shown in Table 3.

TABLE 3

| Phase | Ingredients | % w/w |
|---|---|---|
| A. | Beeswax (WHITE BEESWAX)[1] | 9.00 |
|  | Hydrogenated Olive Oil (and) *Olea Europaea* (Olive) Fruit Oil (and) *Olea Europaea* (Olive) Fruit Oil Unsaponifiables (OLIWAX)[2] | 12.00 |
|  | *Copernicia Cerifera* (Carnauba) Wax (CARNAUBA T-3)[1] | 3.00 |
|  | *Crambe Abyssinica* Seed Oil, and Shea Butter extract (FANCOR ABYSEA)[3] | 15.00 |
|  | Meadowfoam Estolide (FANCOR MEADOWESTOLIDE)[3] | 3.00 |
|  | *Prunus Amygdalus Dulcis* (Almond) Seed Oil (SWEET ALMOND OIL)[4] | 12.00 |
|  | *Ricinus Communis* (Castor) Seed Oil (CASTOR OIL)[5] (q.s. to 100%) | 15.00 |
|  | Luvitol ® Lite (Hydrogenated Polyisobutene)[6] | 10.00 |
| B. | *Crambe Abyssinica* Seed Oil (FANCOR ABYSSINIAN OIL)[3] | 10.00 |
|  | Chione ™ HD Crystal Mint S830V (Synthetic Fluorphlogopite (and) Titanium Dioxide)[6] | 3.00 |
|  | Chione ™ M SVA[6] | 7.00 |
|  | Duocrome ® GY 227C (Mica (and) Titanium Dioxide (and) Iron Oxides (and) Ferric Ferrocyanide)[6] | 1.00 |
|  | Antioxidants | q.s. |
|  | Preservatives | q.s. |

[1]Koster Keunen, LLC
[2]B&T Company
[3]Fancor Ltd.
[4]Jeen International Corporation
[5]Alzo International Inc.
[6]BASF The concealer stick composition can be prepared according to the following steps.
I. Pre-disperse Phase B
II. Weigh all Phase A ingredients in a vessel and heat to 85±3° C., stirring until melted and uniform.

III. Add premixed Phase B to Phase A, maintaining temperature at 82±3° C. for 30 minutes with gentle agitation. (This will allow de-aeration if vacuum is not available).

IV. Reduce temperature to 75±3° C.

V. Pour into molds.

An exemplary cream foundation composition is shown in Table 4.

TABLE 4

| Phase | Ingredients | % w/w |
| --- | --- | --- |
| A. | DI Water (q.s to 100%) | 60.60 |
|  | Methylpropanediol (MPDIOL Glycol)[1] | 5.00 |
|  | Magnesium Aluminum Silicate (VEEGUM)[2] | 0.60 |
|  | Xanthan Gum (KELTROL CG-T)[3] | 0.40 |
| B. | Cetearyl Olivate (and) Sorbitan Olivate (OLIVEM 1000)[4] | 4.00 |
|  | Hydrogenated Olive Oil (and) *Olea Europaea* (Olive) Fruit Oil (and) *Olea Europaea* (Olive) Oil Unsaponifiables (OLIWAX)[4] | 2.00 |
|  | Caprylic/Capric Triglyceride (and) Di-PPG-3 Myristyl Ether Adipate (and) Sorbitan Isostearate (CRODASPERSE)[5] | 7.00 |
|  | Meadowfoam Estolide (and) Meadowfoam Delta-Lactone (MEADOWDERM 100)[6] | 2.00 |
|  | Isodecyl Neopentanoate (CERAPHYL SLK)[7] | 5.00 |
|  | Antioxidants | q.s. |
|  | Preservatives | q.s. |
| C. | Kaolin (HUBER 90)[8] | 0.50 |
|  | Polymethyl Methacrylate (PMMA H)[9] | 4.00 |
|  | Chione ™ M SVA[10] | 3.00 |
|  | Chione ™ HD Metric Violet S530V (Synthetic Fluorphlogopite (and) Titanium Dioxide)[10] | 1.90 |
|  | Chroma-Lite ® Brown CL4509 (Mica (and) Bismuth Oxychloride (and) Iron Oxides)[10] | 4.00 |

[1]Lyondell Chemical Company
[2]RT Vanderbilt, Inc.
[3]CP Kelco
[4]B&T Company
[5]CRODA
[6]Fancor Ltd.
[7]ISP
[8]J.M. Huber Corporation
[9]Brenntag Specialties, Inc
[10]BASF The cream foundation composition can be prepared according to the following steps.

I. Add DI Water and MPDIOL Glycol to main vessel and begin homogenization.

II. Sprinkle in VEEGUM and homogenize until uniform.

III. Sprinkle in the KELTROL CG-T and homogenize until uniform.

IV. In a separate container, heat Phase B to 60-70° C. and mix until uniform.

V. Under homogenization add Phase B to Phase A at 70° C.

VI. Pulverize Phase C in appropriate blending equipment.

VII. Under homogenization, sprinkle Phase C to Phase AB until uniform color is achieved. Then, sweep mix.

VIII. Drop batch at 40° C.

An exemplary composition for a deodorant stick is shown in Table 5.

TABLE 5

| Phase | Ingredients | % w/w |
| --- | --- | --- |
| A. | DI Water (q.s. to 100%) | 17.70 |
|  | Propylene Glycol | 59.20 |
|  | PEG-200 Hydrogenated Castor Oil/IPDI Copolymer (POLYDERM PPI-CO-200)[1] | 12.00 |
|  | Sodium Stearate (JEECHEM Sodium Stearate)[2] | 8.00 |
|  | Isosteareth-2 (HETOXOL IS-2)[3] | 2.00 |
|  | UV Absorbers | q.s. |
| B. | Chione ™ M SVA[4] | 1.00 |
|  | Cellini ® Blue 620CB1C (Mica (and) Titanium Dioxide (and) Blue 1 Lake (and) Hydrogenated Polyisobutene (and) Palmitic Acid)[4] | 0.10 |
| C. | Fragrance | q.s |

[1]Alzo International Inc.
[2]Jeen International Corporation
[3]Global Seven Inc.
[4]BASF The deodorant composition can be prepared according to the following steps.

I. Mix Propylene Glycol and water and heat to 80-85° C.

II. Add Polyderm in small increments until all is melted and dissolved.

III. Add Sodium Stearate and maintain temperature at 85° C. until solution is clear.

IV. Add Isosteareth-2 Alcohol and mix well.

V. Pre-disperse Phase B and add to Phase A.

VI. Add Phase C to Phase A-B and mix until uniform.

VII. Fill into appropriate containers.

An exemplary eyeliner composition is shown in Table 6.

TABLE 6

| Phase | Ingredients | % w/w |
| --- | --- | --- |
| A. | DI Water (q.s to 100%) | 56.25 |
|  | Luviset ® Clear (VP/Methacrylamide/Vinyl Imidazole Copolymer)[1] | 20.00 |
|  | D-Panthenol 75W (Panthenol)[1] | 1.00 |
|  | Glycerin (and) Glyceryl Acrylate/Acrylic Acid Copolymer (and) Propylene Glycol (and) PVM/MA Copolymer (LUBRAJEL OIL)[2] | 10.00 |
|  | Antioxidants | q.s. |
|  | Preservatives | q.s. |
| B. | Xanthan Gum (KELTROL CG-T)[3] | 1.50 |
| C. | Cloisonné ® Vivid Red 450DHCB (Mica (and) Iron Oxides (and) Titanium Dioxide (and) Silica)[1] | 10.00 |
|  | Chione ™ M SVA | 1.25 |

[1]BASF
[2]ISP
[3]CP Kelco

The eyeliner composition can be prepared according to the following steps.

I. In a suitable container add all Phase A ingredients.

II. Sprinkle Phase B into Phase A while being rapidly agitated.

III. Add Phase C to Phase AB and homogenize until uniform.

*Note: Cold process.

An exemplary hair gloss composition is shown in Table 7.

TABLE 7

| Phase | Ingredients | % w/w |
|---|---|---|
| A. | PEG-7 Glyceryl Cocoate (TEGOSOFT GC)[2] | 8.00 |
|  | Cremophor ® A 25 (Ceteareth-25)[1] | 22.00 |
|  | Cremophor ® WO 7 (PEG-7 Hydrogenated Castor Oil)[1] | 1.00 |
|  | Propylene Glycol | 3.00 |
|  | PEG-8 Methicone (MASIL SF 19 CG)[3] | 1.00 |
|  | MultiReflections™ Soft Sparkle Orchid 580P (Mica (and) Titanium Dioxide (and) Silica)[1] | 0.15 |
|  | Chione ™ M SVA[1] | 0.75 |
| B. | DI Water (q.s to 100%) | 64.00 |
| C. | Fragrance (VERBENA MINT YY06-01079)[4] | 0.10 |
|  | Preservatives | q.s. |

[1]BASF
[2]Evonik Goldschmidt GmbH
[3]The Lubrizol Corporation
[4]Ungerer & Company The hair gloss composition can be prepared according to the following steps.
I. Add Phase A ingredients in above order at 80° C. and mix until uniform. Assure each is dissolved prior to next addition.
II. Heat Phase B to 80° C. and combine with Phase A.
III. Cool to 50° C. while allowing air bubbles to rise out and foam to dissolve. Add fragrance and preservative.
IV. Pour into containers while liquid and allow to set at room temperature.

An exemplary icy gel toothpaste composition is shown in Table 8.

TABLE 8

| Phase | Ingredients | % w/w |
|---|---|---|
| A. | DI Water (q.s. to 100%) | 6.00 |
|  | Sorbitol (LIPONIC 70-NC)[1] | 54.30 |
|  | Glycerin | 10.00 |
|  | Cellulose Gum | 0.50 |
|  | PEG-32 (CARBOWAX PEG 1450)[2] | 3.00 |
| B. | DI Water | 5.00 |
|  | Sodium Benzoate | 0.30 |
|  | Sodium Saccharin | 0.20 |
| C. | Hydrated Silica (ZEODENT 165)[3] | 5.00 |
|  | Hydrated Silica (ZEODENT 113)[3] | 15.00 |
| D. | Flavor (Sweet Mint # 26037G)[4] | 0.15 |
|  | Blue 1 (0.5% Aqueous Solution) | 0.10 |
|  | Chione ™ M SVA[5] | 0.45 |

[1]Lip Chemicals, Inc.
[2]Dow Chemical Company
[3]J.M. Huber Corporation
[4]Shaw Mudge & Company
[5]BASF The icy gel toothpaste composition can be prepared according to the following steps.
I. Pre-mix Water, Sorbitol and Glycerin, and disperse Cellulose Gum with mixing until thoroughly dispersed.
II. Add PEG-32 and heat to 50° C.
III. At 40° C. add pre-mixed Phase B to Phase A while mixing until completely uniform.
IV. Add Phase C to Phase A-B while under agitation.
V. Add Phase D ingredients one by one to Phase A-B-C mixing until completely uniform.
VI. Fill into appropriate containers.

An exemplary lip balm composition is shown in Table 9.

TABLE 9

| Phase | Ingredients | % w/w |
|---|---|---|
| A. | Pentaerythrityl Tetraisostearate (CRODAMOL PTIS)[1] (q.s to 100%) | 20.05 |
|  | Ricinus Communis (Castor) Seed Oil | 11.60 |
|  | Di-PPG-3 Myristyl Ether Adipate (CROMOLLIENT DP3A)[1] | 11.50 |
|  | Crambe Abyssinica Seed Oil (FANCOR ABYSSINIAN OIL)[2] | 10.50 |
|  | C10-30 Cholesterol/Lanosterol Esters (SUPER STEROL ESTER)[1] | 6.25 |
|  | Meadowfoam Estolide (MEADOWESTOLIDE)[2] | 6.00 |
|  | Meadowfoam Estolide (and) Meadowfoam Delta-Lactone (and) Crambe Abyssinica Seed Oil (and) Carthamus Tinctorius (Safflower) Seed Oil (and) Olive Oil Unsaponifiable (and) Beta-Sitosterol (ANTI-AGING SKIN COMPLEX)[2] | 5.00 |
|  | Euphorbia Cerifera (Candelilla) Wax (Candelilla Wax SP 75)[3] | 8.00 |
|  | Copernicia Cerifera (Carnauba) Wax (Carnauba Wax SP 63)[3] | 2.00 |
|  | Ozokerite (Ozokerite Wax White SP 1026)[3] | 3.00 |
|  | Microcrystalline Wax (MULTIWAX 180-W)[3] | 3.00 |
|  | Antioxidants | q.s. |
|  | Preservatives | q.s. |
|  | Fragrance | q.s. |
|  | Uvinul ® MC80 (Octinoxate)[4] | 5.00 |
|  | Oxybenzone | 4.00 |

TABLE 9-continued

| Phase | Ingredients | % w/w |
|---|---|---|
| B. | Chione ™ M SVA[4] | 1.00 |
|  | Chione ™ HD Digital Pink S430V (Synthetic Fluorphlogopite (and) Titanium Dioxide)[4] | 2.00 |
|  | Red 40* | 1.10 |
| C. | Fragrance | q.s |

[1]CRODA
[2]Fancor Ltd.
[3]Strahl & Pitsch, Inc.
[4]BASF

The lip balm composition can be prepared according to the following steps.
  I. Weigh all of Phase A ingredients in a vessel and heat to 85±3° C., stirring until melted and uniform.
  II. Add premixed Phase B to Phase A maintaining temperature at 82±3° C. for 30 minutes with gentle agitation. (This will allow de-aeration if vacuum is not available).
  III. Cool to 75±3° C. and add fragrance and pour into container.
  Note: If iron oxide or organic pigments are used, they should first be dispersed in Ricinus Communis (Castor) Seed Oil; this mixture should then be milled in either a colloid or roller mill.

An exemplary crème lipstick composition is shown in Table 10.

TABLE 10

| Phase | Ingredients | % w/w |
|---|---|---|
| A. | *Crambe Abyssinica* Seed Oil (FANCOR ABYSSINIAN OIL)[1] (q.s to 100%) | 18.86 |
|  | *Euphorbia Cerifera* (Candelilla) Wax (Candelilla Wax SP 75)[2] | 3.00 |
|  | *Copernicia Cerifera* (Carnauba) Wax (Carnauba Wax SP 63)[2] | 1.50 |
|  | Beeswax (Beeswax White SP 422)[2] | 1.00 |
|  | Ceresine (Ceresine Wax White SP 252)[2] | 6.00 |
|  | Microcrystalline Wax (MULTIWAX 180-W)[2] | 1.50 |
|  | Oleyl Alcohol (NOVOL)[3] | 3.00 |
|  | Isosteryl Palmitate (JEECHEM ISP)[4] | 4.25 |
|  | Caprylic/Capric Triglyceride | 8.25 |
|  | Bis-Diglyceryl Polyacyladipate-2 (SOFTISAN 649)[5] | 2.00 |
|  | Acetylated Lanolin Alcohol (JEELAN MOD)[4] | 2.50 |
|  | Sorbitan Tristearate (JEECHEM STS)[4] | 1.75 |
|  | Ozokerite (Ozokerite Wax White SP 1026)[2] | 6.75 |
|  | Glyceryl Monolaurate (ULTRAPURE GML)[6] | 1.00 |
|  | Antioxidants | q.s. |
|  | Preservatives | q.s. |
|  | UV Absorbers | q.s. |
| B. | Meadowfoam Estolide (MEADOWESTOLIDE)[2] | 2.00 |
|  | Pentaerythrityl Tetraisostearate (CRODAMOL PTIS)[3] | 6.00 |
| C. | *Crambe Abyssinica* Seed Oil (FANCOR ABYSSINIAN OIL)[1] | 20.00 |
|  | Red 21* | 3.14 |
|  | Chione ™ M SVA[7] | 1.50 |
|  | Chione ™ HD Pixel White S130S (Synthetic Fluorphlogopite (and) Titanium Dioxide)[7] | 3.00 |
|  | Chione ™ Snowfall White S130D (Synthetic Fluorphlogopite (and) Titanium Dioxide)[7] | 3.00 |
| D. | Fragrance | q.s. |

[1]Fancor Ltd.
[2]Strahl & Pitsch, Inc.
[3]CRODA
[4]Jeen International Corporation
[5]SASOL
[6]Ultra Chemical, Inc.
[7]BASF The crème lipstick composition can be prepared according to the following steps.
  I. Weigh all of Phase A ingredients in a vessel and heat to 85±3° C., stirring until melted and uniform.
  II. Pre-disperse Phase B to Phase A, maintaining temperature at 82±3° C. for 30 minutes with gentle agitation.
  III. Cool to 75±3° C. and add fragrance.
  IV. Pour into container or components. *Note: If iron oxide or organic pigments are used, they should first be dispersed in Crambe Abyssinica Seed Oil; this mixture should then be milled in either a colloid or roller mill.

An exemplary eye mascara composition is shown in Table 11.

TABLE 11

| Phase | Ingredients | % w/w |
|---|---|---|
| A. | Caprylyl Methicone (DOW CORNING TORAY FZ-3196)[1] | 4.00 |
|  | Lauryl PEG/PPG-18/18 Methicone (DOW CORNING 5200 FORMULATION AID)[1] | 6.00 |
|  | *Copernicia Cerifera* (Carnauba) Wax (No. 1 Yellow Carnauba Wax)[2] | 3.00 |
|  | C30-45 Alkyldimethylsilyl Polypropylsilsesquioxane (DOW CORNING SW-8005 C30 RESIN WAX)[1] | 2.00 |
|  | Caprylic/Capric Triglyceride (JEECHEM CTG)[3] | 3.00 |
|  | Uvinul ® A Plus B* (Ethylhexyl Methoxycinnamate (and) Diethylamino Hydroxybenzoyl Hexyl Benzoate)[4] | 0.10 |
|  | Preservatives O/S | q.s. |
|  | Vitamin E Acetate Care (Tocopheryl Acetate)[4] | 0.25 |
| B. | Isododecane (and) Disteardimonium Hectorite (and) Propylene Carbonate (BENTONE GEL ISD V)[6] | 6.00 |
|  | Polymethyl Methacrylate (PMMA S)[7] | 5.00 |
|  | Isododecane (Permethyl 99A)[5] (q.s to 100%) | 25.00 |
|  | Chione ™ M SVA[4] | 1.00 |
|  | Flamenco ® Summer Gold 230Q (Mica (and) Titanium Dioxide)[4] | 5.00 |

TABLE 11-continued

| Phase | Ingredients | % w/w |
|---|---|---|
| C. | DI Water | 17.65 |
| | Propylene Glycol | 2.00 |
| | Preservatives W/S | q.s. |
| D. | Luviset ® Shape (Polyacrylate-22)[4] | 20.00 |

[1]Dow Corning Corporation
[2]Frank B. Ross Company, Inc.
[3]Jeen International Corporation
[4]BASF
[5]Presperse LLC
[6]Elementis Specialties
[7]Brenntag Specialties Inc.

The eye mascara composition can be prepared according to the following steps.
 I. In main vessel heat Phase A ingredients to 60° C. with continuous mixing.
 II. In a side vessel premix Phase B into Phase A maintaining temperature to 60° C.
 III. In a side vessel premix Phase C and heat to 50° C.
 IV. Add Phase C to Phase AB under homogenization. Sweep mix and reduce heat to 50° C.
 V. Add Phase D to Phase ABC.
 VI. Package into appropriate containers.
 *Uvinul® A Plus B is not an approved Sunscreen active in the USA & Canada.
 **When Carbon Black pigments are used, they should first be dispersed in Isododecane and BENTONE Gel ISD V this mixture should then be milled in either a colloid or roller mill.

An exemplary nail enamel composition is shown in Table 12.

TABLE 12

| Phase | Ingredients | % w/w |
|---|---|---|
| A | Nail Enamel Base (Butyl Acetate (and) Toluene (and) Nitrocellulose (and) Tosylamide/Formaldehyde Resin (and) Isopropyl Alcohol (and) Dibutyl Phthalate (and) Ethyl Acetate (and) Camphor (and) n-Butyl Alcohol (and) Silica (and) Quaterinum-18 Hectorite) | 97.70 |
| B | Iron Oxides (Black, 4.0-6.0% Toluene Free/Formaldehyde Free Color Solutions) | 0.10 |
| | Flamenco ® Winter Sparkle 130Q (Mica (and) Titanium Dioxide)[1] | 0.25 |
| | Chione ™ M SVA[1] | 1.25 |
| | Cloisonné ® Satin Bronze 250M (Mica (and) Iron Oxides)[1] | 0.70 |

[1]BASF

The nail enamel composition can be prepared according to the following steps.
 I. Add Phase A in an appropriate size vessel fitted with a propeller mixer.
 II. Add Phase B to Phase A mixing until batch is uniform.
 III. Fill into containers.

An exemplary pressed powder eyeshadow composition is shown in Table 13.

TABLE 13

| Phase | Ingredients | % w/w |
|---|---|---|
| A. | Chione ™ M SVA[1] (q.s. to 100%) | 21.50 |
| | Kaolin (HUBER 90)[2] | 15.00 |
| | Microcrystalline Cellulose (AVICEL PC 105)[3] | 12.50 |
| | Chroma-Lite ® Bronze CL4499 (Mica (and) | 10.00 |

TABLE 13-continued

| Phase | Ingredients | % w/w |
|---|---|---|
| | Bismuth Oxychloride (and) Iron Oxides)[1] | |
| | Flamenco ® Summer Gold 230Q (Mica (and) Titanium Dioxide)[1] | 19.50 |
| | Cloisonné ® Orange 363C (Mica (and) Titanium Dioxide (and) Iron Oxides)[1] | 8.50 |
| B. | *Crambe Abyssinica* Seed Oil (and) *Butyrospermum Parkii* (Shea Butter) Extract (FANCOL ABYSHEA)[4] | 7.50 |
| | *Simmondsia Chinensis* (Jojoba) Seed Oil | 1.50 |
| | *Cocos Nucifera* (Coconut) Oil | 1.00 |
| | Antioxidant | q.s. |
| | Preservatives | q.s. |
| C. | Flamenco ® Summer Gold 230Q (Mica (and) Titanium Dioxide)[1] | 3.00 |

[1]BASF
[2]J.M. Huber Corporation
[3]FMC Corporation
[4]Fancor Ltd.

The pressed powder eyeshadow composition can be prepared according to the following steps.
 I. Thoroughly blend Phase A in appropriate dry blending/dispersing equipment.
 II. Pre-disperse Phase B until uniform.
 III. Spray Phase B into Phase A. Pulverize and return to blender.
 IV. Add Phase C to Phase AB. Tumble until uniform.
 V. Press.

An exemplary shampoo composition is shown in Table 14.

TABLE 14

| Phase | Ingredients | % w/w |
|---|---|---|
| A. | DI Water (q.s. to 100%) | 15.36 |
| | Acrylates/Aminoacrylates/C10-30 Alkyl PEG-20 Itaconate Copolymer (STRUCTURE PLUS)[1] | 7.00 |
| B. | DI Water | 15.00 |
| | Cocamide MEA (COMPERLAN 100)[2] | 0.50 |
| C. | Sodium Laureth Sulfate (TEXAPON NSO)[2] | 35.70 |
| | Cocamidopropyl Betaine (TEGO BETAIN L 7)[3] | 13.50 |
| | Disodium Laureth Sulfosuccinate (REWOPOL SBFA 30B)[3] | 7.80 |
| | Luviquat ® Sensation (Polyquaternium-87)[4] | 1.84 |
| | Preservatives | q.s. |
| | Fragrance (Spring Flower # 0794029)[5] | 0.50 |

TABLE 14-continued

| Phase | Ingredients | % w/w |
|---|---|---|
|  | Reflecks ® Shinny Bronze G270L (Calcium Sodium Borosilicate (and) Iron Oxides)[4] | 0.10 |
|  | Chione ™ M SVA[4] | 0.10 |
|  | Blue 1 (1% Aqueous Solution) | 0.25 |
| D. | Citric Acid (10% Aqueous Solution) | 2.35 |

[1]Akzo Nobel Surface Company
[2]COGNIS
[3]Goldschmidt GmbH
[4]BASF
[5]Bell Flavors & Fragrances, Inc.

The shampoo composition can be prepared according to the following steps.
I. Weigh out components of Phase A and Phase B separately and stir until the solution is homogeneous.
II. Add Phase B to Phase A and stir until uniform.
III. Add Phase C to Phase AB and stir until uniform.
IV. Adjust pH to 5.6 with citric acid with constant stirring.

An exemplary spray highlighter composition is shown in Table 15.

TABLE 15

| Phase | Ingredients | % w/w |
|---|---|---|
| A. | SD Alcohol 40 B (Alcohol Denatured)[2] | 55.00 |
|  | Aminomethyl Propanol (AMP-95)[3] | 0.88 |
|  | MEA Borate (and) MIPA Borate (MONACOR BE)[4] | 0.05 |
|  | Uvinul ® MC 80 (Ethyhexyl Methoxycinnamate)[1] | 0.05 |
|  | Cyclopentasiloxane (DOW CORNING 245 Fluid)[5] | 0.10 |
|  | D-Panthenol 75W (Panthenol)[1] | 0.10 |
|  | Cucumber TEA 862157 (Fragrance)[6] | 0.10 |
|  | Luvimer ® 100P (Acrylates Copolymer)[1] | 2.00 |
|  | Ultrahold ® Strong (Acrylates Copolymer)[1] | 3.00 |
| B. | Chione ™ M SVA[1] | 0.10 |
|  | Cloisonné ® Monarch Gold 233X (Mica (and) Titanium Dioxide (and) Iron Oxides)[1] | 0.70 |
|  | Chione ™ HD Infinite White S130V (Synthetic Fluorphlogopite (and) Titanium Dioxide)[1] | 0.20 |
| C. | Hydrofluorocarbon 152A[7] | 37.72 |

[1]BASF
[2]AAPER Alcohol and Chemical Co.
[3]Dow Chemical Company
[4]CRODA
[5]Dow Corning Corporation
[6]Drom Fragrances, Inc.
[7]DuPont Company The spray highlighter composition can be prepared according to the following steps.
I. Mix all ingredients in order shown with adequate agitation.
II. Fill into appropriate containers and charge with propellant.
Aerosol Density: 0.85 g/mL
Vapor Pressure @ ambient: 55 psig
The spray highlighter composition can be packaged as follows.
Can: Exal Aluminum Epoxy Lined
Valve: Seaquist Perfect Valve XT-96
Body: XT ES BRB 013 ORIF N
Stem: 0.013 Virgin Nylon
Actuator: XT-150 ES 0.013 Misty
Diptube: 0.165 ID"

EXAMPLES

The products, methods of their manufacture and methods of use are further described in detail by reference to the following experimental examples. These examples are provided for purposes of illustration only, and are not intended to be limiting unless otherwise specified. Thus, the compositions and methods of use should in no way be construed as being limited to the following examples, but rather, should be construed to encompass any and all variations which become evident as a result of the teaching provided herein.

Example 1

To characterize the heavy metal composition of synthetic mica (with no metal oxide coating), heavy metal analysis was performed on two samples of CHIONE™ synthetic mica. The data are shown in Table 16.

TABLE 16

| Metal | Synthetic mica- Sample 1 | Synthetic mica- Sample 2 |
|---|---|---|
| Arsenic | <0.25 ppm | 0.26 ppm |
| Barium | <25 ppm | <24 ppm |
| Cadmium | <0.25 ppm | <0.24 ppm |
| Cobalt | 0.59 ppm | 0.52 ppm |
| Chromium | 1.5 ppm | 2.0 ppm |
| Copper | <24.6 ppm | <24.4 ppm |
| Mercury | <0.10 ppm | <0.10 ppm |
| Nickel | 3.1 ppm | 2.5 ppm |
| Lead | <0.25 | 0.54 |
| Antimony | <0.25 ppm | <0.24 ppm |

The heavy metal analysis of synthetic mica showed that it contained less than 1 ppm lead. This result is especially important for cosmetic applications around the lip area.

Example 2

The M-fraction of CHIONE™ synthetic mica (with no metal oxide coating) was used in this example. The particle size distribution (PSD) of this fraction was: D10=2-4 micrometers (μm); D50=6-8 μm; D90 15-20 μm.

The synthetic mica was coated in three different concentrations of Nε-lauroyl-L-lysine solution: 4.5%, 7.5% and 10%. The Nε-lauroyl-L-lysine (hereinafter "lauroyl lysine") used in this example is commercially available as Amihope® LL (Ajinomoto NA, Fort Lee, N.J.). Amihope® LL is described by the manufacturer as a functional powder that is not soluble in water or oil, and is soluble in alkaline solutions. The three lauroyl lysine solutions for this example were prepared in a 3.5% NaOH solution. Solutions were stirred for 15 minutes at 350 rpm.

A 32% calcium chloride ($CaCl_2$) solution was prepared in deionized water.

The details for coating the synthetic mica with 10.0% lauroyl lysine are as follows, and were carried out at ambient conditions. In a 5 liter flask, 150 grams M-fraction synthetic mica and 1350 grams deionized water were combined. Mixing speed was set to 600 rpm, then 24.6 grams of 32% $CaCl_2$ was added. The solution was then stirred for 30 minutes, after which the lauroyl lysine solution was added using a peristaltic pump and a pH relay controller. 1365 grams 10% lauroyl lysine was added, while maintaining pH between 5.8-6.2 using 10% HCl. Rates for both the lauroyl lysine addition and the 10% HCl addition were about 5 grams/minute. After the addition of the lauroyl lysine, the pH was adjusted to pH 7.

The coated platy substrate was filtered and washed with a total of 3000 ml deionized water (6×500 ml). The washed coated platy substrate was dried at 120° C. to a constant weight, which took about 3 hours. After drying, the coated platy substrate was sieved using a #200 mesh screen.

The substantially same procedure was used to coat the synthetic mica with 4.5% and 7.5% lauroyl lysine. For the 4.5%, after the addition of the lauroyl lysine, the pH was adjusted to pH 7, and then the coated platy substrate was filtered and washed. The 4.5% coated substrate was dried at 110° C. to a constant weight, which took about 2 hours.

The contact angle of the three resulting coated platy substrates was measured. In general, the greater that contact angle, the greater the hydrophobicity of the surface. A contact angle of greater than 90° is designated a hydrophobic surface. The contact angle data is summarized in Table 17.

TABLE 17

| Lauroyl lysine coating | Average Contact Angle after 2 min |
|---|---|
| No coating | Wetted with angle <90° |
| 4.5% | 137.6° |
| 7.5% | 138.1° |
| 10.0% | 135.7° |

The uncoated synthetic mica had a contact angle of less than 90°, indicative of its hydrophilic surface. All three coated synthetic mica samples had a contact angle greater than 90° and therefore are hydrophobic.

Example 3

To characterize the treated synthetic mica, cosmetic compositions were prepared with the treated synthetic mica. As comparative samples, the compositions were also prepared using the following platy substrates: untreated CHIONE synthetic mica M-fraction; untreated natural mica (Natural V mica); and lauroyl lysine-treated natural mica (MEARLMICA® Treated SVA, BASF; comprises 2.5-4.5% lauroyl lysine).

A lipstick composition comprising 3% of a platy substrate. The lipsticks were tested on skin and lip. The lipsticks comprising coated substrates were found to have a preferable feeling.

Pressed powder compositions were also prepared. The composition was a formulation known to have rough texture. The composition comprises 20.0% platy substrate and was evaluated on skin. A noticeable difference was observed for the pressed powder compositions comprising treated substrates compared to the compositions comprising untreated substrates. As with the lipsticks, the pressed powders comprising coated substrates had a preferable feeling.

Other benefits of the treated synthetic mica were observed. It has a high oil absorption. This property can prevent sweating in lipstick applications. The treated synthetic mica compositions possessed a very smooth, almost creamy, feeling. The treated synthetic mica compositions also exhibited good skin adhesion.

Lipsticks made with either talc or MEARLMICA® Treated SVA have a "dirty" mass tone. In contrast, lipsticks made with treated synthetic mica did not exhibit the same degree of "dirty" mass tone. A visual color shift was observed in the treated CHIONE lipstick compared to the MEARLMICA® Treated SVA lipstick. Thus, the treated synthetic mica was notable for being more transparent in the lipstick formulas.

Lipstick compositions comprising "5 micron" pigments, such as REFLECKS can have a gritty feeling on the lips. It was found that in a lipstick composition comprising treated synthetic mica and 5 micron REFLECKS Gilded Gold G232L (a multilayer metal oxide-coated borosilicate substrate pigment manufactured by BASF), the lauroyl lysine treated synthetic mica used at a 1:1 ratio masked the grittiness feeling of the 5 micron Reflecks on the lips. In contrast, MEARLMICA® Treated SVA did not mask as well the gritty feeling in a comparable lipstick formulation on the lips. Thus, the treated synthetic mica advantageously exhibits improved function of masking a gritty feeling from particulate components such as pigments in a cosmetic, as compared to treated natural mica.

Example 4

Compressibility of lauroyl lysine-coated CHIONE™ M-fraction synthetic mica was assessed. Compressibility was also assessed for: uncoated synthetic mica M-fraction; uncoated natural mica (Natural V mica); lauroyl lysine-coated natural mica (MEARLMICA® Treated SVA); and SUPAFINO H talc. Compressibility was assessed as follows. A 3 gram sample of platy substrate was placed in a standard large round eyeshadow pan press and placed in an eyeshadow press. The sample was pressed at 2500 psi for 10 seconds. The hardness and tactile properties of the resulting pad of pressed platy substrate was then assessed. The hardness was tested using a Zwick/Durotester (durometer). Hardness values ranges from 0 (for full penetration) to 100 (for no penetration), wherein full penetration is between 2.46 and 2.54 mm (0.097 to 0.1 in).

The treated synthetic platy substrate had a hardness rating of 63. In contrast, lower hardness ratings were measured for both MEARLMICA® Treated SVA and for talc. These data indicate that the pressed pads of MEARLMICA® Treated SVA and of talc were softer and less compact. Moreover, the pressed pads of treated CHIONE™ M fraction synthetic mica were more uniform, compared to the untreated substrates. In addition, it was found that the coated substrates compressed at a lower pressure than the untreated substrates. Thus, the treated synthetic mica advantageously exhibits improved hardness and compressibility compared to MEARLMICA® Treated SVA.

Example 5

Figure 1:
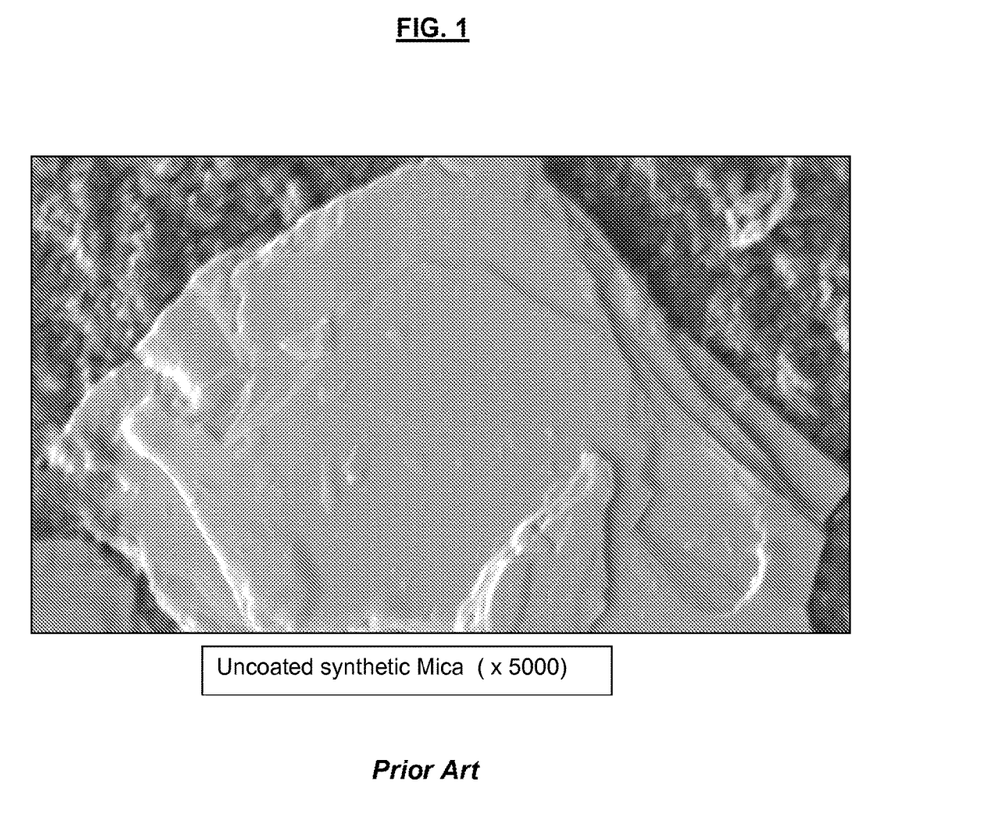
FIG. 1 is a scanning electron microscopy image of synthetic mica. Magnification is 5000×.

Scanning electron microscopy images were taken of: CHIONE™ synthetic mica (without lauroyl lysine coating): CHIONE™ synthetic mica coated with 5% lauroyl lysine in a process substantially similar to that described above; and CHIONE™ synthetic mica in a physical blend with 5% lauroyl lysine. The images are shown in FIGS. 1-3, respectively.

Figure 2:
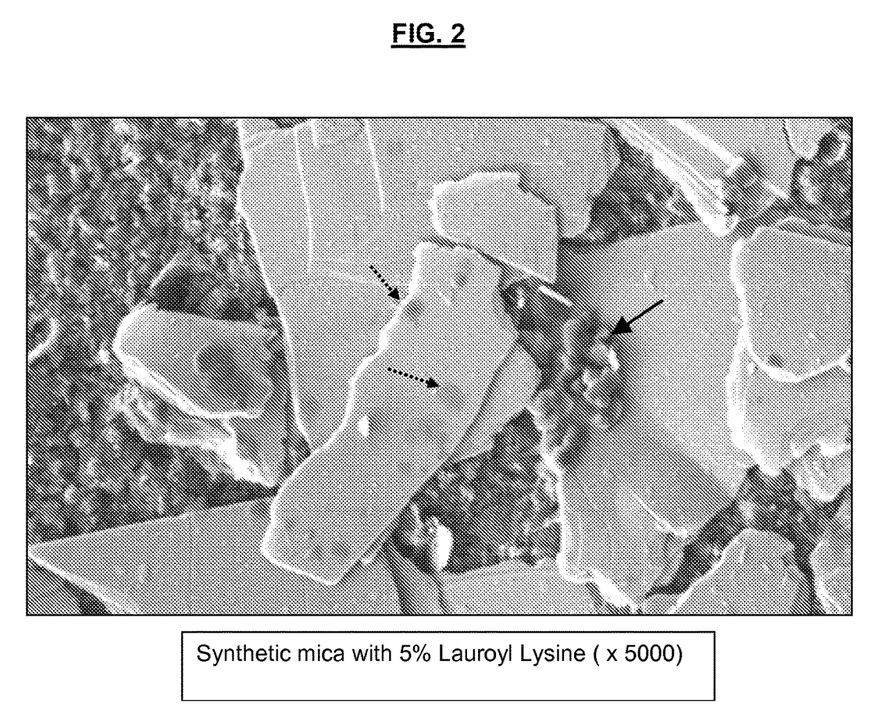
FIG. 2 is a scanning electron microscopy image of synthetic mica coated with 5% lauroyl lysine. Magnification is 5000×. Dotted arrows indicate areas of coated lauroyl lysine on the synthetic mica. Solid arrow indicates precipitated lauroyl lysine particles.
Figure 3:
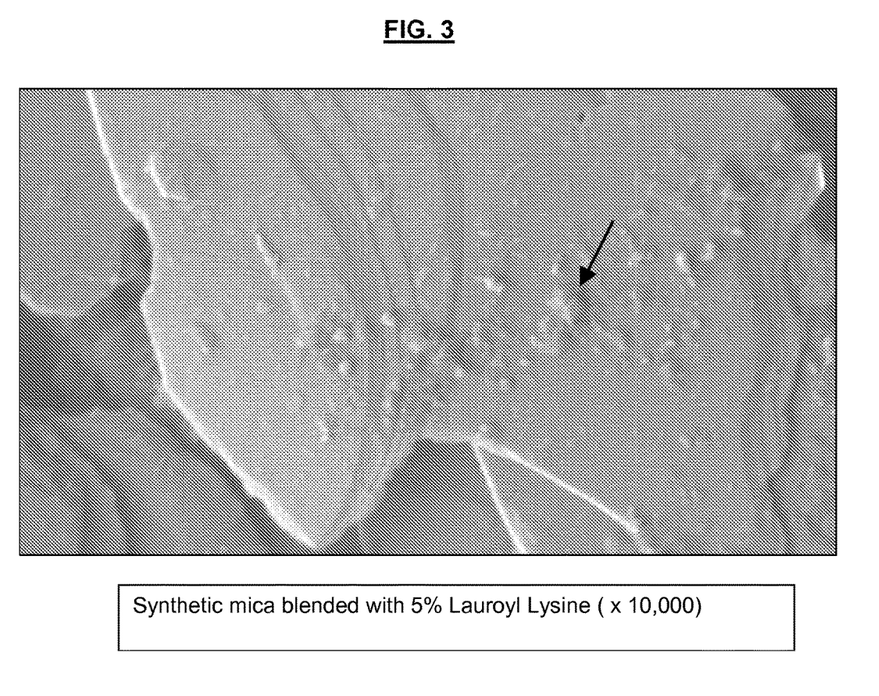
FIG. 3 is a scanning electron microscopy image of synthetic mica blended with 5% lauroyl lysine. Magnification is 10,000×. Solid arrow indicates lauroyl lysine particles resting on surface of synthetic mica

FIG. 2 illustrates that lauroyl lysine precipitated onto the synthetic mica in a smooth precipitate form. FIG. 3 illustrates that in a simple physical blend of synthetic mica and lauroyl lysine, lauroyl lysine appears to form rough particles that rest on the surface of the synthetic mica.

Example 6

Whiteness of a treated platy substrate of the disclosure and of uncoated, Natural V mica was assessed in accordance with ASTM E313 Standard Guide for Measuring Whiteness. The treated platy substrate was CHIONE™ synthetic mica (about 90 to 96%) with a coating of about 4% to 10% lauroyl lysine.

Figure 4:
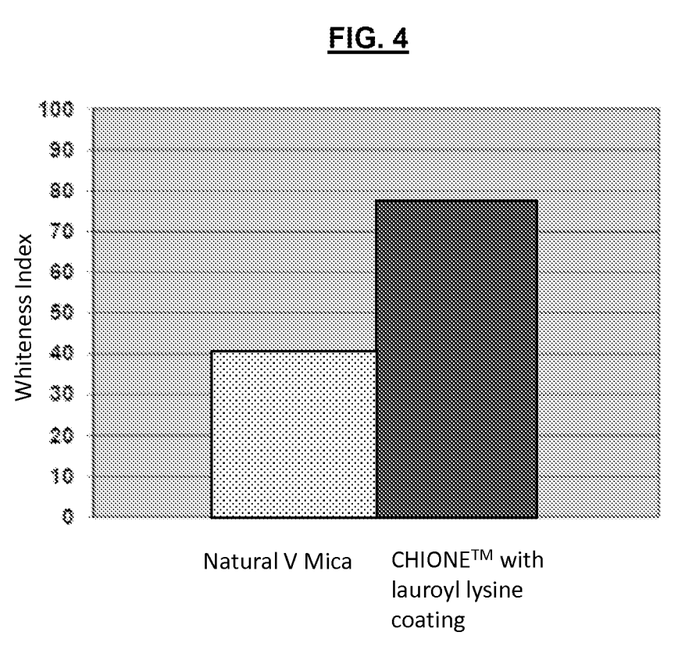
FIG. 4 is a graph depicting whiteness data for a representative treated platy substrate of the disclosure and for untreated Natural V mica.

On the whiteness index, the Natural V mica had a whiteness of about 40. The treated platy substrate had a whiteness of over 70. See FIG. 4.

Example 7

To assess the smoothness of the treated platy substrate of the disclosure, the static coefficient of friction (Tan θ) was measured in accordance with ASTM G115-10 Standard Guide for Measuring and Reporting Friction Coefficients. The lower the coefficient of friction, the smoother the material.

Three samples were assessed. The control sample (no pigment), untreated CHIONE™ synthetic mica, and CHIONE™ synthetic mica treated with lauroyl lysine. The data are depicted in Table 18.

TABLE 18

|  | Slide angle θ (average of three) | Static Coefficient of Friction (Tanθ) |
| --- | --- | --- |
| Control | 29.3° | 0.56 |
| 20% untreated CHIONE ™ synthetic mica | 22.7° | 0.42 |
| 20% CHIONE ™ synthetic mica treated with lauroyl lysine | 16.3° | 0.29 |

The treated platy substrate of the disclosure had a notably lower coefficient of friction compared to the untreated platy substrate. Thus, the treated platy substrate is a much smoother material than the corresponding untreated platy substrate. This property is advantageous for cosmetic applications of the treated platy substrate.

The disclosures of each and every patent, patent application, and publication cited herein are hereby incorporated herein by reference in their entirety.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

It is understood that any and all whole or partial integers between any ranges set forth herein are included herein.

While the products, methods of making them, and their methods of use have been disclosed with reference to specific embodiments, it is apparent that other embodiments and variations may be devised by others skilled in the art without departing from the true spirit and scope of the described products and methods. The appended claims are intended to be construed to include all such embodiments and equivalent variations.

What is claimed is:

1. A cosmetic composition comprising a treated platy substrate comprising a platy substrate coated with Nε-lauroyl-L-lysine and a particulate component having a gritty feeling and wherein the treated platy substrate is present in an amount sufficient to mask the gritty feeling;
   wherein:
   the platy substrate is synthetic mica without a metal oxide coating that comprises ≤0.26 ppm arsenic; ≤25 ppm barium; ≤0.25 ppm cadmium; ≤0.59 ppm cobalt; ≤2.0 ppm chromium; ≤24.6 ppm copper; ≤0.10 ppm mercury; ≤3.1 ppm nickel; ≤1.0 ppm lead; and ≤0.25 ppm antimony; and
   a particle size distribution of the treated platy substrate ranges from about 15 μm to about 90 μm.

2. The composition of claim 1, wherein the Nε-lauroyl-L-lysine coating is present on the surface of the platy substrate in the range of about 0.5% to about 15% by weight of the platy substrate.

3. The composition of claim 2, wherein the Nε-lauroyl-lysine coating is present on the surface of the platy substrate in the range of about 4% to about 6% by weight of the platy substrate.

4. The composition of claim 1, wherein the treated platy substrate has a thickness from about 0.1 μm to about 10 μm.

5. The composition of claim 1, wherein the composition further comprises at least one auxiliary agent.

6. The composition of claim 1, wherein the composition further comprises one or more of octyldodecyl neopentanoate, meadowfoam estolide, methylpropanediol, magnesium aluminum silicate, xanthan gum, isodecyl neopentanoate, polymethyl methacrylate, pentaerythrityl tetraisostearate, bis-diglyceryl polyacyladipate-2, acetylated lanolin alcohol, sorbitan tristearate, caprylyl methicone, isododecane, sodium laureth sulfate, cocamidopropyl betaine, disodium laureth sulfosuccinate, aminomethyl propanol, and cyclopentasiloxane.

\* \* \* \* \*